United States Patent [19]

Moss et al.

[11] Patent Number: 5,741,249
[45] Date of Patent: Apr. 21, 1998

[54] ANCHORING TIP ASSEMBLY FOR MICROWAVE ABLATION CATHETER

[75] Inventors: Jon F. Moss, Antioch; Peter Sturzu, Cupertino; Hiep P.H. Nguyen, Fremont, all of Calif.

[73] Assignee: Fidus Medical Technology Corporation, Fremont, Calif.

[21] Appl. No.: 755,998

[22] Filed: Nov. 25, 1996

[51] Int. Cl.⁶ ................................................. A61B 17/39
[52] U.S. Cl. .............................. 606/33; 606/41; 607/101; 607/154; 607/156
[58] Field of Search ...................... 606/33, 41; 607/154, 607/156, 119, 122, 101, 126, 127, 128, 100

[56] References Cited

U.S. PATENT DOCUMENTS

| | | | |
|---|---|---|---|
| 3,976,082 | 8/1976 | Schmitt | 607/128 |
| 4,033,357 | 7/1977 | Helland et al. | 607/126 |
| 4,244,371 | 1/1981 | Farin . | |
| 4,409,993 | 10/1983 | Furihata . | |
| 4,416,276 | 11/1983 | Newton et al. . | |
| 4,465,079 | 8/1984 | Dickhudt | 607/128 |
| 4,494,539 | 1/1985 | Zenitani . | |
| 4,601,296 | 7/1986 | Yerushalmi . | |
| 4,641,649 | 2/1987 | Walinsky et al. . | |
| 4,657,015 | 4/1987 | Irnich . | |
| 4,800,899 | 1/1989 | Elliott . | |
| 4,825,880 | 5/1989 | Stauffer et al. . | |
| 4,841,988 | 6/1989 | Fetter et al. . | |
| 4,924,863 | 5/1990 | Sterzer . | |
| 4,945,912 | 8/1990 | Langberg . | |
| 5,019,076 | 5/1991 | Yamanashi et al. . | |
| 5,045,056 | 9/1991 | Behl . | |
| 5,097,845 | 3/1992 | Fetter et al. . | |
| 5,100,388 | 3/1992 | Behl et al. . | |
| 5,129,396 | 7/1992 | Rosen et al. . | |
| 5,150,717 | 9/1992 | Rosen et al. . | |
| 5,172,699 | 12/1992 | Svenson et al. . | |
| 5,188,122 | 2/1993 | Phipps et al. . | |
| 5,190,054 | 3/1993 | Fetter et al. . | |
| 5,230,349 | 7/1993 | Langberg . | |
| 5,246,438 | 9/1993 | Langberg . | |
| 5,300,068 | 4/1994 | Rosar et al. . | |

(List continued on next page.)

FOREIGN PATENT DOCUMENTS

| | | |
|---|---|---|
| WO93/08757 | 5/1993 | WIPO . |
| WO93/20767 | 10/1993 | WIPO . |
| WO93/20768 | 10/1993 | WIPO . |
| WO93/20886 | 10/1993 | WIPO . |
| WO93/20893 | 10/1993 | WIPO . |
| WO 96/36397 | 11/1996 | WIPO . |

OTHER PUBLICATIONS

Landberg et al., "Catheter Ablation of the Atrioventricular Junction Using a Helical Microwave Antenna: A Novel Means of Coupling Energy to the Endocardium", vol. 14, Dec. 1991, pp. 2105–2113.

Primary Examiner—John P. Lacyk
Assistant Examiner—David M. Ruddy
Attorney, Agent, or Firm—Beyer & Weaver, LLP

[57] ABSTRACT

An ablation catheter with an anchoring tip extension includes an elongated flexible tubular member adapted to be inserted into a vessel in the body of a patient. A transmission line is disposed within the tubular member, and a transducer is coupled to the transmission line for generating an electric field sufficiently strong to cause tissue ablation. An anchoring tip extension, which is located at the distal end of the catheter, lodges into the wall of a cardiac chamber and serves to anchor the catheter both during an ablation procedure and during the process of conforming the catheter to the wall. In one preferred embodiment, the catheter includes a shape memory wire. In another embodiment, the transmission line of the catheter is a co-axial cable, and the transducer is a helical antenna coil that is adapted to radiate electromagnetic energy in the microwave frequency range. Methods for manufacturing and using such ablation catheters are also described.

21 Claims, 7 Drawing Sheets

U.S. PATENT DOCUMENTS

| | | |
|---|---|---|
| 5,300,099 | 4/1994 | Rudie . |
| 5,314,466 | 5/1994 | Stern et al. . |
| 5,364,336 | 11/1994 | Carr . |
| 5,364,392 | 11/1994 | Warner et al. . |
| 5,370,644 | 12/1994 | Langberg . |
| 5,370,677 | 12/1994 | Rudie et al. . |
| 5,383,922 | 1/1995 | Zipes et al. . |
| 5,405,346 | 4/1995 | Grundy et al. . |
| 5,507,802 | 4/1996 | Imran ........................ 607/128 |
| 5,575,810 | 11/1996 | Swanson et al. .............. 128/642 |
| 5,582,609 | 12/1996 | Swanson et al. .............. 606/33 |

ANCHORING TIP ASSEMBLY FOR MICROWAVE ABLATION CATHETER

CROSS REFERENCE TO RELATED APPLICATION

U.S. patent application Ser. No. 08/732,045, filed Oct. 16, 1996, is related to the present application and is incorporated by reference herein in its entirety.

BACKGROUND OF THE INVENTION

1. Field of Invention

The present invention relates generally to ablation catheter systems that use electromagnetic energy in the microwave frequencies to ablate internal bodily tissues. More particularly, an ablation catheter with an anchoring tip assembly and a method for manufacturing such an ablation catheter are disclosed.

2. Description of the Prior Art

Catheter ablation has recently become an important therapy for the treatment of cardiac arrhythmias, cardiac disrhythmias and tachycardia. Most approved ablation catheter systems now utilize radio frequency (RF) energy as the ablating energy source. However, RF energy has several limitations including the rapid dissipation of energy in surface tissues which results in shallow "burns" and a failure to access deeper arrhythmic tissues. As such, catheters which utilize electromagnetic energy in the microwave frequency range as the ablation energy source are currently being developed. Microwave frequency energy has long been recognized as an effective energy source for heating biological tissues and has seen use in such hyperthermia applications as cancer treatment and preheating of blood prior to infusions. Catheters which utilize microwave energy have been observed to be capable of generating substantially larger lesions than those generated by RF catheters, which greatly simplifies the actual ablation procedures. Some catheter systems which utilize microwave energy are described in the U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stern, et al, each of which is incorporated herein by reference.

Atrial fibrillation is one type of cardiac arrhythmia which may be treated using catheter ablation. Cardiac arrhythmias are generally circuits, known as "arrhythmia circuits," which form within the chambers of the heart. As is known to those skilled in the art, arrhythmia circuits are abnormal electrical connections which may form in various areas of the heart. For example, arrhythmia circuits may form around veins and/or arteries which lead away from and to the heart. Cardiac arrhythmia's may occur in any area of the heart where arrhythmia circuits are formed.

Atrial fibrillation occurs in the atria of the heart, and more specifically at the region where pulmonary veins are located, atrial fibrillation may occur. In atrial fibrillation, arrhythmia circuits form within the atria and between pulmonary veins. Due to the fact that these arrhythmia circuits prevent the heart from beating normally, cutting the arrhythmia circuits is necessary to restore a normal heart beat. Many different cutting patterns may be implemented to cut arrhythmia circuits and, specifically, arrhythmia circuits formed within the atria.

FIG. 1a is a diagrammatic illustration of one cutting pattern for arrhythmia circuits. This particular cutting pattern is well-suited for use in cutting arrhythmia circuits formed around pulmonary veins. That is, this cutting pattern may be used in atrial fibrillation applications. FIG. 1a shows cross-sections of pulmonary veins 110. It should be appreciated that the orientation of pulmonary veins 110 as shown is exaggerated for illustrative purposes. Arrhythmia circuits (not shown), or connections, may form between pulmonary veins 110. In order to eliminate the circuits, thereby eliminating unwanted, or abnormal, electrical connections in the heart, circuits between pulmonary veins 110 may be cut. As shown, cutting-lines 116, 118 may be formed between and around pulmonary veins 110 in order to cut circuits formed between pulmonary veins 110. These cutting-lines 116, 118 are essentially lesions which disrupt arrhythmia circuits formed within the atria of the heart. In the described embodiment, cutting-lines 116, 118 form linear lesions. In other embodiments, cutting-lines 116, 118 may not necessarily form linear lesions. Also, as shown, cutting-lines 116 are formed orthogonally to cutting-lines 118, although cutting-lines formed between and around pulmonary veins 110 may take on any suitable orientation.

FIG. 1b is a diagrammatic illustration of a second cutting pattern for arrhythmia circuits. As shown, FIG. 1b illustrates a second cutting pattern which may be used to cut arrhythmia circuits formed around pulmonary veins for atrial fibrillation applications. Cross-sections of pulmonary veins 110 are shown with cutting-lines 126, 130 formed between adjacent pulmonary veins 110. By way of example, cutting-line, or lesion, 126a is formed between adjacent pulmonary veins 110a and 110b. Similarly, cutting-line 130a is formed between adjacent pulmonary veins 110a and 110c. As will be appreciated by those skilled in the art, although cutting-lines 126, 130 have been drawn "through" pulmonary veins 110, the pulmonary veins 110 are not actually cut through. Rather, the arrhythmia circuits (not shown) formed between pulmonary veins 110 are cut through.

The process of positioning a catheter in different locations within a heart chamber is often inefficient, as conventional catheters often must be removed and repositioned for each ablation process. For example, referring back to FIG. 1b, conventional ablation catheters are often completely removed from the atrium after cutting-line 130a is created in order to reposition the catheter to create cutting-line 130b. This is often necessary because the process of positioning the catheter in order to form cutting-line 130a often results in a bending of the catheter tip, or the portion of the catheter which contains an antenna, as the catheter tip conforms to the wall of the atrium. Once the catheter tip is bent, it becomes difficult to precisely position the tip, as the already bent tip must be conformed to another portion of the atrium. Further, if a catheter tip is not appropriately anchored against the wall of the atrium, for example, applying any force to the catheter tip in order to allow the catheter tip to conform to the wall may result in the catheter tip slipping from the desired position. Specifically, if the distal portion of the catheter tip is not properly anchored against the wall of the atrium, precisely positioning the catheter tip may be difficult, as the catheter tip may be dislodged from the desired position. Slippage has the tendency to occur especially when the wall of the heart is uneven, i.e. when there are crevices in the wall. Any slippage of the catheter tip from a desired location requires a repositioning of the catheter tip. At times, if the catheter tip is bent, it may be necessary to remove the catheter from a person's body prior to repositioning the catheter tip. This process is inefficient, as it prolongs the duration of an ablation procedure. Accordingly, it would be desirable to have a catheter tip which may be securely anchored and therefore does not have the tendency to slip under the application of force.

SUMMARY OF THE INVENTION

To achieve the foregoing and in accordance with the purpose of the present invention, an ablation catheter with an anchoring tip extension is disclosed. The ablation catheter includes an elongated flexible tubular member adapted to be inserted into a vessel in the body of a patient. A transmission line is disposed within the tubular member, and a transducer is coupled to the transmission line for generating an electric field sufficiently strong to cause tissue ablation. An anchoring tip extension, which is located at the distal end of the catheter and is more flexible than the elongated flexible tubular member, lodges into the wall of a cardiac chamber and serves to anchor the catheter both during an ablation procedure and during the process of conforming the catheter to the wall. In one preferred embodiment, the anchoring tip extension has a diameter of approximately 0.60 inches and a length in the range of approximately 0.2 to 0.3 inches In another embodiment, the anchoring tip extension is formed from a silicon material. In still another embodiment, the transmission line of the catheter is a co-axial cable, and the transducer is a helical antenna coil that is adapted to radiate electromagnetic energy in the microwave frequency range.

A method for manufacturing an ablation catheter with an anchoring tip extension involves attaching an antenna coil having a longitudinal axis to a transmission line. The antenna coil is then filled with a first dielectric material in a molding operation, and the anchoring tip extension, which is carried on the distal end of the catheter, is formed in a second molding operation. Positioning ribs, which are used to orient the filled antenna coil in a mold which is used to encapsulate the filled antenna coil with a second dielectric material, may be created with the first dielectric material such that the positioning ribs are aligned along the longitudinal axis of the antenna coil.

In one embodiment, the distal end of the catheter is an extension plug. In such an embodiment, the method for manufacturing the ablation catheter may further involve inserting sensor leads through the antenna coil along the longitudinal axis of the antenna coil and creating the extension plug at the distal end of the antenna coil using the first dielectric material. Further, in such an embodiment, sensors attached to the sensor leads are mounted over the extension plug.

A method for medical treatment using an ablation catheter system that includes a catheter tip with a transmission line, a transducer, and an anchoring tip extension involves introducing the catheter into a patient's body such that the anchoring tip extension is positioned in a crevice in the wall of a cardiac chamber. Once the anchoring tip extension is positioned, the distal portion of the catheter is substantially conformed to a wall of the chamber. Electromagnetic energy may then be applied to the transmission line to cause ablation of cardiac tissue. When the anchoring tip extension is repositioned, and the catheter tip is reconformed to the wall, cardiac tissue may be ablated as required.

The method for medical treatment may also include monitoring electro-physiological signals using catheter electrodes, determining an appropriate ablation position based at least in part on the monitored electro-physiological signals, and positioning the transducer at the determined appropriate ablation position. In one preferred embodiment, microwave energy is applied to the transmission line to cause the ablation.

BRIEF DESCRIPTION OF THE DRAWINGS

The invention, together with further advantages thereof, may best be understood by reference to the following description taken in conjunction with the accompanying drawings in which:

FIG. 2b is a diagrammatic cross-sectional view of the conformally positionable ablation catheter tip of FIG. 2a.

FIG. 5b is a diagrammatic longitudinal side view of the conformally positionable antenna assembly of FIG. 5a.

DETAILED DESCRIPTION OF THE DRAWINGS

A presently preferred conformally positionable microwave ablation catheter system with an anchoring tip extension in accordance with the present invention will be described below making reference to the accompanying drawings. A conformally positionable microwave ablation catheter with an anchoring tip extension is capable of anchoring in a crevice, as for example a crevice in the wall of a cardiac chamber, thereby preventing the catheter from slipping when force is applied to the catheter. With the anchoring tip extension lodged, or anchored, in a crevice, force is applied to the catheter such that the catheter conforms to the wall of the cardiac chamber. A shape memory wire positioned at a distal portion, i.e. catheter tip, of the catheter enables the catheter to conform to and, upon repositioning, reconform to the wall of the cardiac chamber without the need for removing the catheter tip from a patient's body for straightening.

Figure 1A:
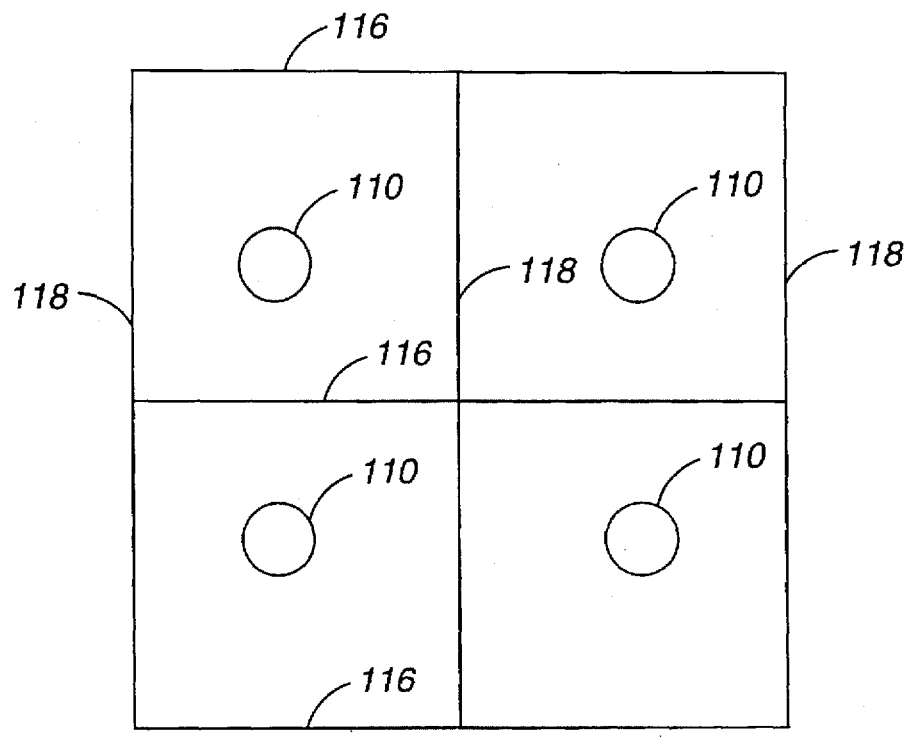
FIG. 1a is a diagrammatic illustration of one cutting pattern for circuits around pulmonary veins.
Figure 1B:
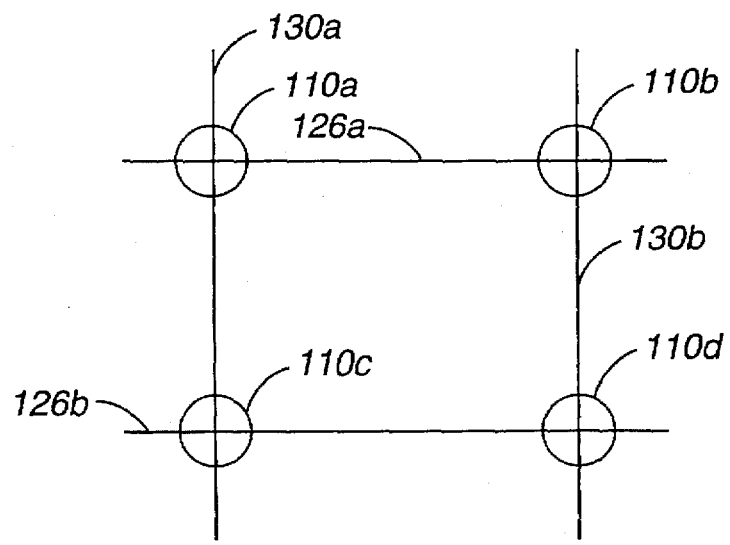
FIG. 1b is a diagrammatic illustration of another cutting pattern for circuits around pulmonary veins.
Figure 2A:
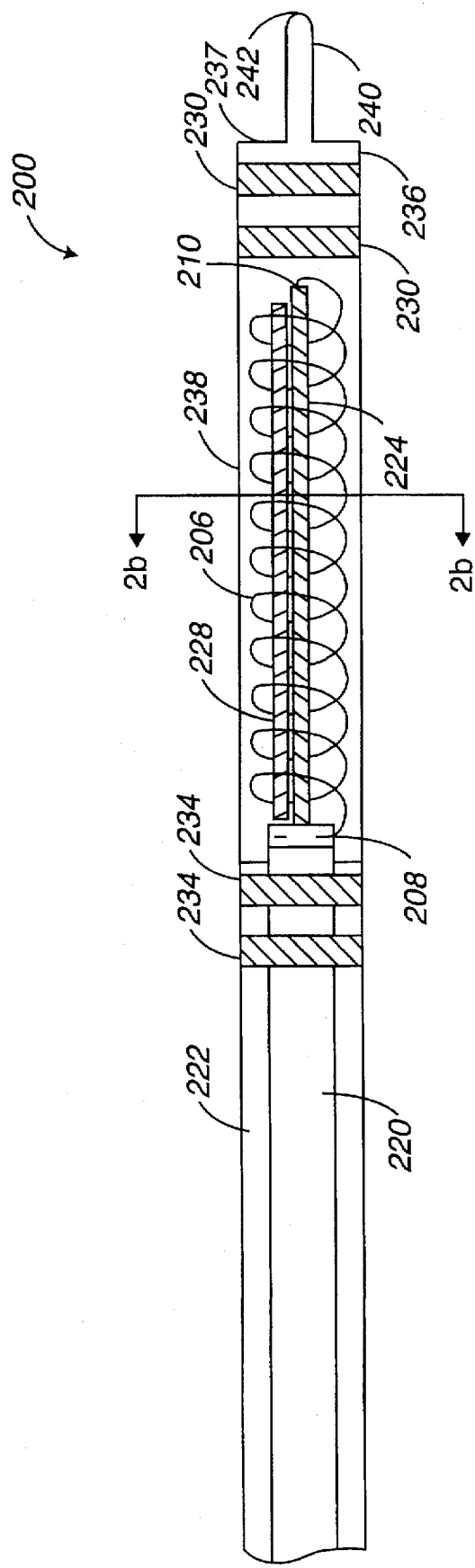
FIG. 2a is a diagrammatic longitudinal cross-sectional view of a conformally positionable ablation catheter tip with an anchoring tip extension in accordance with an embodiment of the present invention.
Figure 2B:
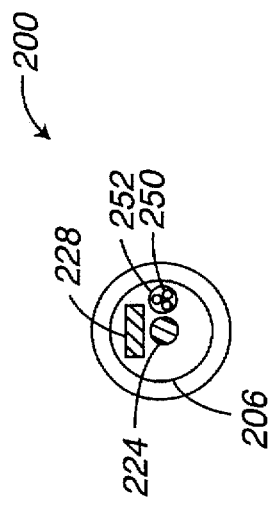

As seen in FIGS. 2a and 2b, a conformally positionable ablation catheter 200 generally includes an antenna 206 with a proximal end 208 and a distal end 210. Proximal end 208 of antenna 206 is grounded by a shield (not shown) of transmission line 220. It should be appreciated that transmission line 220, which is supported within a distal shaft 222, is typically coupled to a power supply (not shown) which is external to catheter 200. Distal end 210 of antenna 206 is attached to center conductor 224 of transmission line 220. Typically, antenna 206 is in the form of a coil, i.e. an antenna coil, which is made from any suitable material, such as spring steel, beryllium copper, or silver-plated copper. The outer diameter of antenna coil 206 will vary to some extent based on the particular application of the catheter. By way of example, a catheter suitable for use in an atrial fibrillation application may have typical coil outer diameters in the range of approximately 0.07 to 0.1 inches. More preferably, the outer diameter of antenna coil 206 may be in the range of approximately 0.08 to 0.09 inches.

In the embodiment as shown, a shape memory metal wire 228, is axially located within antenna, or antenna coil, 206. For embodiments in which antenna 206 is not in the form of an antenna coil, shape memory metal wire 228 may be positioned such that longitudinal axes of both antenna 206 and shape memory metal wire 228 are aligned. Shape memory metal wire 228, which is a flat wire, may be made from any suitable shape memory metal. The shape of shape memory metal 228 is dependent upon the desired positioning attributes of catheter 200. A shape memory metal is a moldable metal which has a "default," or rest, state. This default state may also be considered to be a neutral state. A shape memory metal is generally a metal which may be shaped when force is applied to the metal. However, when force is removed from a shape memory metal, the metal returns to the default state, which is the original state the metal was in prior to the application of force. While the shape memory metal may be any suitable "elastic" metal, nickel titanium, copper beryllium alloys, and steel alloys have been observed to work well.

As previously mentioned, the typical shape of shape memory metal wire 228 is a flat shape, e.g. it has a rectangular cross-section where the height of the rectangle is much greater than the width of the rectangle. In general, a flat shape may be considered to be any shape in which the average height of the shape is significantly greater than the average width of the shape. A flat-shaped shape memory metal wire 228 is preferred due to the fact that a flat-shaped shape memory metal wire 228 will have the tendency to bend at one axis, or in one plane. Hence, a flat-shaped shape memory metal wire 228 is easier to control, and, therefore, easier to steer since the flat-shaped shape memory metal wire 228 will not exhibit significant bending in more than one plane. However, although flat cross-sectional shapes are preferred for shape memory metal wire 228, other shapes such as round wires will also work in many applications.

In embodiments which include distal electrodes 230 as illustrated in FIG. 2a, sensor conduit 252, shown in FIG. 2b (shown in more detail in FIG. 5b), which carries sensor wires 250, shown in FIG. 2b, is generally located along the longitudinal axis of catheter 200. In other words, sensor conduit 252 which carries sensor wires 250 is typically axially located within antenna coil 206. In this case, the term "axially located" refers to sensor conduit 252 being located such that is parallel to the longitudinal axis of antenna coil 206. The sensor wires are connected with distal electrodes 230 which are provided as part of catheter tip 200 to facilitate positioning of catheter 200 during use. Distal electrodes 230 are used to detect electro-physiological signals from cardiac tissue and, hence, may be used to map the relevant region of the heart prior to or after an ablation procedure. Distal electrodes 230 may also be used to aid in positioning catheter 200 during the ablation procedure. Distal electrodes 230 may be made from a variety of biocompatible materials, which include stainless steel or iridium platinum. Like distal electrodes 230, proximal electrodes 234, which are typically formed from the same biocompatible materials as distal electrodes 230, may also be used for positioning purposes and to map regions of the heart prior to or after an ablation procedure.

The distal portion 236 of catheter 200, which includes the elongated tube portion 238 of catheter 200, i.e. the section of catheter 200 which encapsulates antenna 206, may be formed from a flexible dielectric material. That is, the material which both fills and surrounds antenna coil 206 is typically a flexible dielectric material. Suitable flexible dielectric materials include, but are not limited to, materials such as silicone. One family of silicone products which has been observed to work well is GE Liquid Injection Material (LIM) 6040 through 6071, a silicone family from General Electric in Waterford, N.Y. In general, it is desired for distal tip 236 to be formed from soft, e.g. malleable, materials which are resistant to heat, although in some embodiments, distal tip 236 may be made from Teflon type products.

A flexible tubular member is usually placed or formed over transmission line 220 in a conventional manner. As will be appreciated by those skilled in the art, the flexible tubular member may be made from any suitable material including, but not limited to, medical grade polyolefins, fluoropolymers, or polyvinylidene fluoride. By way of example, PEBAX resins from Autochem of Germany have been used with success.

In general, the dimensions of catheter 200 are dependent upon the requirements of a particular application for catheter 200. However, a catheter tip diameter, e.g. the diameter of elongated tube portion 238, in the range of approximately 7 to 9 French, or approximately 0.092 to 0.141 inches, has been observed to work well for most cardiac applications. It is generally desired that the catheter tip diameter exceed the diameter of the antenna coil, in order to properly encapsulate the antenna coil. By way or example, excess catheter tip in the range of approximately 0.005 to 0.015 inches, as for example approximately 0.01 inches, more than the diameter of the antenna coil work well. A catheter tip length, or the length of catheter tip 200 as measured from approximately the proximal end 208 of antenna 206 to the edge 237 of distal portion 236, in the range of approximately 0.2 to 2.5 inches is preferable. More preferably, a catheter tip length is in the range of approximately 1.2 to 2 inches. The catheter tip length varies as a result of any number of factors which include, but are not limited to, the particular requirements of the application and the size of a patient's heart.

An anchoring tip extension 240 is carried by distal portion 236 of catheter 200, and is generally formed from the same material, i.e. a flexible dielectric material, as the elongated tube portion 238 of catheter 200. Anchoring tip extension 240 may be used to lodge in crevices in the wall of a heart chamber, thereby stabilizing the location of catheter tip 200. In other words, anchoring tip extension 240 may lodge or "hook" in crevices, thereby serving as an anchor to prevent catheter 200 from moving during the course of an ablation procedure.

Anchoring tip extension 240 has axial dimensions which are substantially smaller than the axial dimension, i.e. diameter, of catheter tip 200 which, as previously mentioned, is considered to be the diameter of elongated tube portion 238. An anchoring tip extension diameter, measured away from the distal tip 242 of anchoring tip extension 240, in the range of approximately 0.05 to 0.07 inches, as for example approximately 0.06 inches, is desirable. However, any diameter which is smaller than the diameter of elongated tube portion 238 may be acceptable depending upon the particular catheter application. A preferable length for anchoring tip extension 240 in the range of approximately 0.08 to 0.5 inches, measured from edge 237 of distal portion 236 to distal tip 242 of anchoring tip extension 240, has been shown to work well for lodging purposes. More specifically, a length in the range of approximately 0.12 to 0.4 inches, as for example in the range of approximately 0.2 to 0.3 inches, has been shown to be effective for anchoring purposes. Lengths which are much greater than approximately 0.5 inches have the tendency to be difficult to successfully lodge into crevices in the wall of a heart chamber, for example.

It should be appreciated that anchoring tip extension 240 is generally more flexible than elongated tube portion 238. That is, elongated tube portion 238 is typically stiffer than anchoring tip extension 240. The flexibility of anchoring tip extension 240 enables anchoring tip extension 240 to be readily lodged into crevices, as for example crevices in the wall of a heart chamber. Generally, the smaller diameter of anchoring tip extension 240, as compared with the diameter of elongated tube portion 238, results in greater flexibility in anchoring tip extension 240, as compared to elongated tube portion 238, when both are made from the same material. However, in some embodiments, anchoring tip extension 240 may have substantially the same diameter as elongated tube portion 238, yet anchoring tip extension 240 may be more flexible than elongated tube portion 238. In such embodiments, anchoring tip extension 240 may be created from a different material than elongated tube portion 238.

As shown, edge 237 is "flat." That is, edge 237 is approximately orthogonal to the longitudinal axis of catheter tip 200. However, it should be appreciated that depending upon the nature of the mold and the process used to create anchoring tip extension 240, edge 237 may be curved or angled.

One method for using the described catheter in an ablation procedure will now be described. The catheter may be fed through the femoral artery or any other suitable vessel and into the appropriate region of the heart. By way of example, to treat atrial fibrillation, the catheter tip, which is the distal tip of the catheter, is typically fed into the appropriate atrial chamber. The conformally positionable ablation catheter as described with respect to FIG. 2a has an anchoring tip extension which may be lodged in crevices in the atrial chamber. Lodging the anchoring tip extension in crevices serves to anchor the overall catheter tip, thereby reducing the risk of the catheter tip slipping both while the catheter tip is being conformed to the wall of the chamber and during an ablation procedure.

It should be appreciated that the conformally positionable ablation catheter as described with respect to FIG. 2a may be passively steered. That is, once the distal portion of the catheter is positioned in proximity of a desired position in a chamber of the heart using standard steering methods, the catheter tip may be rotated such that it may reach the desired position. Specifically, as previously described, a flat shape memory metal wire may bend significantly only along one axis, or in one plane. As such, the catheter may have to be rotated such that the "bending-axis" is properly oriented to facilitate the conforming of the catheter tip to the wall of the heart chamber. Once the anchoring tip extension of the catheter tip engages the wall of the heart chamber or a crevice in the wall, a rotation of the catheter tip and the application of force will generally enable the catheter tip to conform to the wall of the heart chamber, while the anchoring tip extension serves to prevent too much non-conformal movement of the catheter tip. That is, the anchoring tip extension, when lodged in a crevice, may prevent any movement of the catheter tip which is not related to movement of the catheter tip which is meant to cause the catheter tip to conform to the wall of the heart chamber. It should be appreciated that any suitable method may be used to apply force to the catheter tip and, hence, the shape memory metal within the catheter tip. One method which may be used to apply force to the catheter tip may entail applying a force by "pushing" or pressing the distal portion of the catheter tip, and, hence, the anchoring tip extension, further against the wall of the heart chamber. The shape memory metal conforms, along with the catheter tip, to the wall of the heart chamber.

With the catheter properly positioned, the electrodes can detect electrical signals in the adjacent regions of the heart. If necessary, the catheter may be further inserted, and or withdrawn to facilitate a mapping of the region of interest. Typically, mapping will indicate the location at which relevant electro-physiological signals, or cardiac signals, as for example EKGs, are strongest. This, in turn, will permit a physician to determine the appropriate ablation position. The catheter is then positioned as necessary to properly locate the antenna for the ablating procedure. After the antenna is properly positioned, microwave energy is applied to the co-axial transmission line to facilitate the ablation. During the ablation procedure, as well as after the operation is completed, the electrodes may be used to monitor the ablation process as well as the results. A suitable microwave generator will be described below with reference to FIG. 7.

When it is desired for the conformally positionable catheter tip to be removed from the wall of the heart chamber or repositioned within the heart chamber, the force pressing the catheter against the heart wall may be at least partially released to enable the catheter to be moved. At least partially releasing the force pressing the catheter against the heart wall also releases at least some of the force on the shape memory metal within the catheter tip. An almost complete removal of force from the catheter tip will enable the shape memory metal and, hence, the catheter tip to return to their original, default shapes. That is, the shape memory metal will return to the state it was in prior to the application of force.

Figure 3:
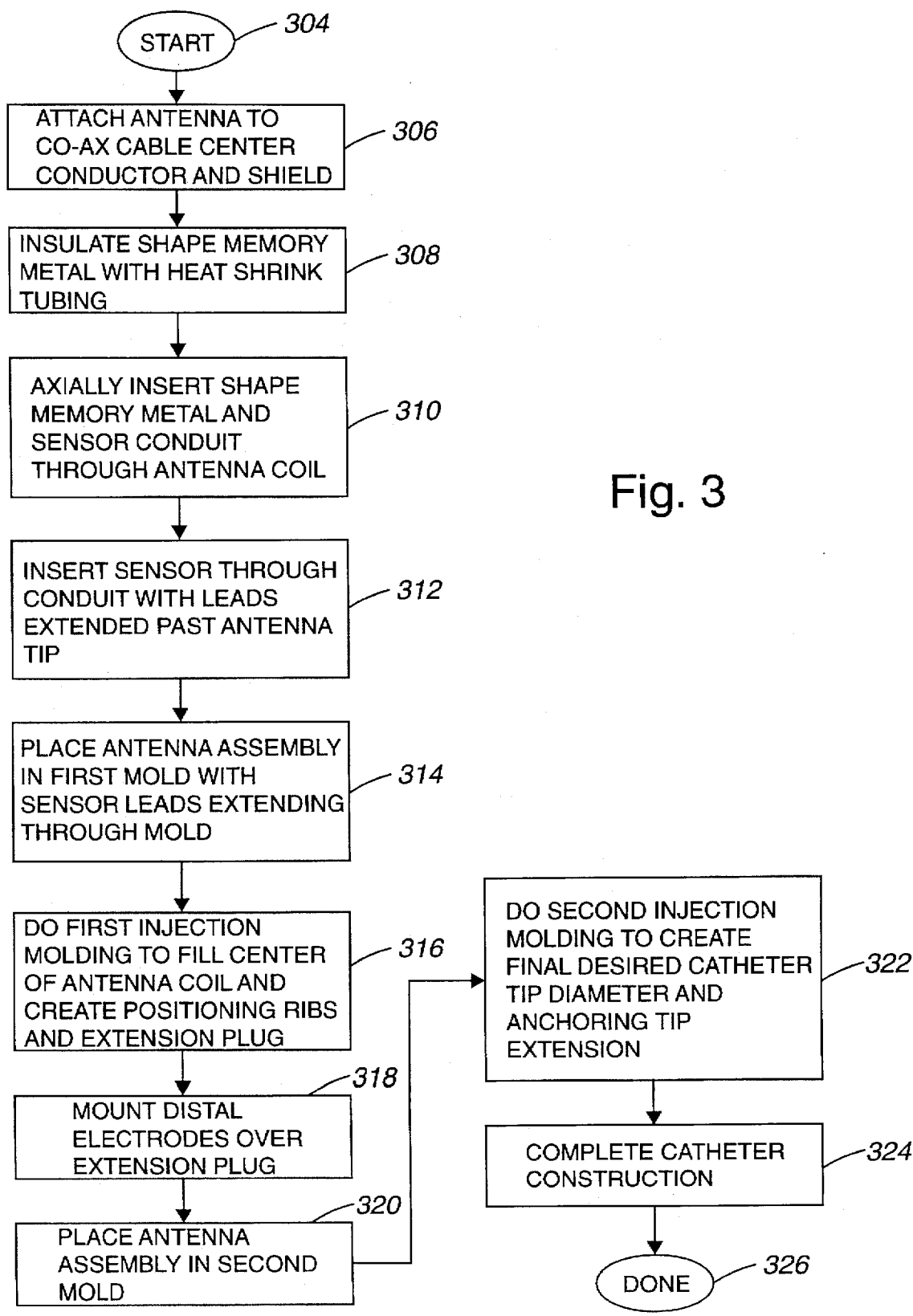
FIG. 3 is a flow chart which illustrates steps in a process for manufacturing a conformally positionable ablation catheter in accordance with an embodiment of the present invention.

Referring next to FIG. 3, a process for manufacturing a conformally positionable ablation catheter with an anchoring tip extension in accordance with one embodiment of the present invention will be described. Initially in step 306, an antenna is attached to the center conductor and the shield of a co-axial cable. It should be appreciated that the co-axial cable is a co-axial transmission line. The distal end of the antenna is connected with the center conductor, while the proximal end of the antenna is grounded to the shield. The antenna may be formed from any suitable material, as for example silver plated copper wire or beryllium copper wire. As will be appreciated by those skilled in the art, the antenna is generally an antenna coil. In the illustrated embodiments, the antenna coil may be helically wound.

A piece of shape memory metal is insulated with heat shrink tubing in step 308 in order to prevent the shape memory metal from shorting against the antenna. The heat shrink tubing is heated and shrunk so that it tightly covers the shape memory metal. As previously described, the shape memory metal may be any suitable "elastic" metal, as for example nickel titanium, a chromium alloy, or a molybdenum alloy. Further, although the shape memory metal is typically elongated with a flat, e.g. rectangular, cross-section, it should be appreciated that the shape memory may take on any number of shapes. By way of example, the shape memory metal may have a round cross-section. A shape memory metal with a flat cross-section is generally preferred, as such a shape memory metal has the tendency to bend in only one direction, i.e. along a single axis, whereas a shape memory metal with a round cross-section may bend in any number of directions.

In step 310, the insulated shape memory metal and a sensor conduit are axially inserted through the antenna coil. That is, the shape memory metal and the sensor conduit are inserted through the antenna coil along the longitudinal axis of the antenna coil. The sensor conduit, which is designed to house sensor leads, may be a polyimide tube. After the shape memory metal and the sensor conduit are properly inserted through the antenna coil, sensor leads are inserted through the sensor conduit such that the leads extend past the tip of the antenna coil in step 312. The sensor leads extend past the tip of the antenna coil to facilitate the attachment of the sensor leads to sensors, which are typically electrodes.

The antenna coil, the sensor conduit with the sensor leads, and the shape memory metal, which together comprise an antenna assembly, are placed in a first mold in step 314. The first mold is generally used to concentrically position the sensor conduit and shape memory metal relative to the antenna coil and to facilitate the creation of positioning ribs along the perimeter of the antenna coil. The first mold, which will be described in more detail below with reference to FIGS. 4a and 4b, has a cavity 404 which supports the antenna coil 412 and, therefore, enables the antenna coil 412 to be filled with a dielectric material. The cavity 404 has a diameter which is substantially equal to the diameter of the antenna coil 412, and is therefore able to support the antenna coil 412 while it is within the cavity 404. The antenna assembly 410 is positioned in the first mold 400 such that the sensor leads 414 extend through the first mold 400. In step 316, a first injection molding operation is performed to fill the center of the antenna coil 412 and to create positioning ribs and an extension plug around the antenna coil 412. That is, a first injection molding operation is essentially used to partially encapsulate the antenna assembly 410. The partially encapsulated antenna assembly 410 will be described below with respect to FIGS. 5a and 5b. Typically, the positioning ribs 510 are formed along the perimeter of the antenna assembly such that the distance from the edge of one positioning rib, as for example edge 512a or positioning rib 510a, to the edge of a directly opposing positioning rib, as for example edge 512c of positioning rib 510c, is equal to the desired, final outer diameter of the completed antenna assembly.

The first injection molding operation may be performed using any suitable pliant material including, but not limited to, silicone. In addition to being flexible when it is cured, silicone is not self-heating, which is a desirable characteristic for a material used in the fabrication of a catheter. One type of silicone which has been observed to work well, as mentioned above, is GE Liquid Injection Material (LIM) 6040, a silicone from General Electric in Waterford, N.Y.

After the first injection molding operation is completed, the distal electrodes 538, if any, are mounted over the extension plug 520 in step 318. A distal electrode 538 is generally a band. However, in the described embodiment, the distal electrodes 538 are annular bands which may be cut into segments after they are mounted, i.e. installed, or the distal electrodes 538 independent segments that form associated bands only after installation. The distal electrodes 538 are connected to the specific sensor, or electrode, leads 537 with which they are associated, thereby forming an electrode ring assembly having the desired number of electrode wires, such as a pair of electrode wires, which may then be slid over the antenna assembly and positioned in its desired location. In some embodiments, heat shrink tubing is then heated and shrunk over the distal electrodes 538 such that the heat shrink tubing tightly covers the electrodes 538 and seals electrode wire holes through which the sensor wires 537 pass. In other embodiments, the distal electrodes 538 may be covered with ultraviolet (UV) curable epoxy which is then cured to set the electrodes 538.

The electrodes 538 are provided to facilitate positioning of the catheter 502 during use. The electrodes 538 are used to detect electro-physiological signals from cardiac tissue and may therefore be used to map the relevant region of the heart prior to or after an ablation procedure. The electrodes 538 may also be used to aid in positioning the catheter 502 for use and to monitor the patient's condition during the ablation process. Although electrodes 538 may be made from a variety of different biocompatible materials, electrodes 538 are typically made of either stainless steel or iridium platinum.

In step 320, the antenna assembly, which, at this point in the process, is partially molded over, is placed in a second mold which is used both to set the final outer diameter of the tip, i.e. the general catheter tip, of the completed antenna assembly, as well as to create an anchoring tip extension at the distal end of the catheter tip. Typically, the distance from the edge of one positioning rib 510 to the edge of a directly opposing positioning rib 510 is approximately equal to final outer diameter of the completed antenna assembly. The second mold, besides being used to set the final outer diameter of the completed antenna assembly and to create the anchoring tip extension, is used to eliminate any bubbles which may have been formed in the catheter as a result of the first injection molding process. The second mold will be discussed in more detail below with reference to FIG. 6.

A second injection molding operation is performed in step 322 to create the final desired diameter of the antenna assembly, or more specifically, the final desired tip diameter of the antenna assembly using the second mold. The second injection molding operation also serves to create an anchoring, or positioning, tip extension at the distal end of the antenna assembly and to eliminate bubbles in the catheter. In embodiments in which there is an extension plug at the distal end of the catheter, the anchoring tip extension is formed at the distal end of the extension plug. The same material which was used in the first injection molding operation is generally also used for the second injection molding operation, though any suitable material may be used. The antenna assembly with the final desired tip diameter and an anchoring tip extension may be considered to be a conformal positioning assembly with an anchoring tip.

After the second injection molding operation is completed, the remaining steps associated with the catheter construction process are performed in step 324. These steps include, but are not limited to, inserting the co-axial cable into a distal shaft, or a flexible tubular member, in a conventional manner. The conventional manner involves binding the antenna assembly to the distal end of the flexible tubular member and attaching a handle to the proximal end of the flexible member. As will be appreciated by those skilled in the art, the flexible tubular member may be made from any suitable material including, but not limited to, medical grade polyolefins, fluoropolymers, or polyvinylidene fluoride. By way of example, PEBAX resins from Autochem of Germany have been used with success in molding the body of the catheter. Stiffening wires, steering wires, additional sensor wires, etc., may all be included in the final assembly as required by a particular design. After the final assembly is completed, the process of manufacturing a conformally positionable catheter with an anchoring tip extension is completed.

Figure 4A:
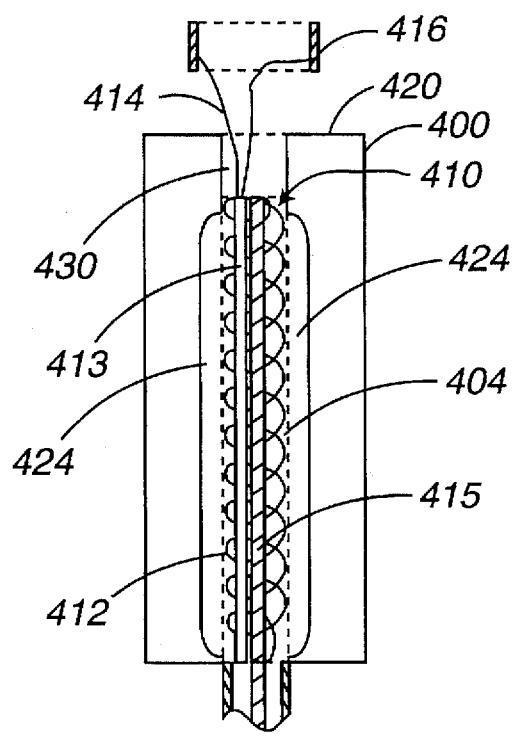
FIG. 4a is a diagrammatic cross-sectional view of an initial mold used to position an antenna assembly during a first molding operation in accordance with an embodiment of the present invention.
Figure 4B:
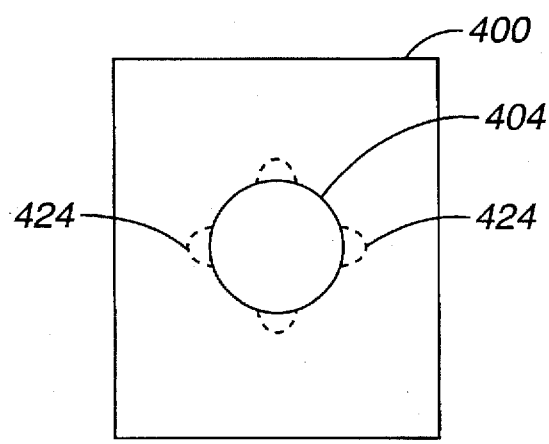
FIG. 4b is a diagrammatic top view of the mold as shown in FIG. 4b.

Referring next to FIGS. 4a and 4b, a mold used to position an antenna assembly will be described in accordance with an embodiment of the present invention. In other words, the mold used in the first injection molding operation as mentioned above with respect to FIG. 3 will be described. FIG. 4a is a diagrammatic cross-sectional view of a mold used to position an antenna assembly, i.e. an antenna, a shape memory wire, and a sensor conduit which houses sensor wires. FIG. 4b is a diagrammatic top view of the mold shown in FIG. 4a. Mold 400, which may be made from any suitable material, has a main cavity 404 in which an antenna assembly 410 is situated. Main cavity 404, as shown, comes into contact with rib cavities 424 which are used to form positioning ribs around antenna assembly 410. Main cavity 404 is further sized such that edges of main cavity, as for example edges 411, come into contact with antenna assembly 410 and, more specifically, an antenna coil 412. That is, the diameter of main cavity 404 is substantially the same as the diameter of antenna coil 412. The shape, or an axial cross-section, of main cavity 404 is dependent upon the desired shape, i.e. axial cross-section, of the molded over antenna assembly (not shown). Typically, the shape of main cavity 404 is either circular (as shown) or oval. However, it should be understood that the shape may be widely varied depending upon the requirements of a particular antenna assembly.

Although only an antenna coil 412 and a sensor conduit 413 with sensor wires 414 have been shown to comprise antenna assembly 410, it should be appreciated that antenna assembly 410 also includes a shape memory wire (not shown) and a transmission line 415. However, purely for ease of illustration, antenna assembly 410 has been generically represented, and the shape memory wire has not been shown in FIG. 4a. Sensor wires 414, which are attached to an electrode ring 416, extend past the top edge 420 of mold 400.

In order to align the components of antenna assembly 410, i.e. antenna coil 412, sensor conduit 413 with sensor wires 414, the shape memory metal (not shown), the transmission line 415, as required for a particular catheter, mechanisms external to mold 400 may be used to hold and otherwise position antenna assembly 410. However, in general, mold 400 is capable of supporting antenna coil 412 for positioning purposes. The shape memory metal and the sensor conduit may suitably be aligned by allowing the shape memory metal and sensor conduit 413 to be held against transmission line 415 within antenna assembly 410. Once the components of antenna assembly 410 are suitably aligned, an injection molding operation which uses any suitable material, as for example silicone as described above with respect to FIG. 3, is implemented to fill the center of antenna coil 412 as well as to create positioning ribs and an extension plug around antenna assembly 410. The positioning ribs are formed using rib cavities 424, while the extension plug is generally formed on antenna assembly 410 near top edge 420 of mold 400 in the top portion 430 of main cavity 404. The extension plug is formed to provide a surface over which electrode ring 416 may be mounted. The diameter of the extension plug after the first molding operation will generally be the equal to the diameter of main cavity 404. In some embodiments, mold 400 may be comprised of at least two distinct pieces which may be interconnected during the molding process, and separated after the molding process in order to remove antenna assembly 410 from mold 400.

In the embodiment as shown, main cavity 404 extends approximately the length of mold 400, while rib cavities 424 extend less than the length of mold 400. As will be appreciated by those skilled in the art, the relative depths, or more generally, dimensions of main cavity 400 and rib cavities 424 may vary greatly depending upon the requirements of a specific antenna assembly.

Figure 5A:
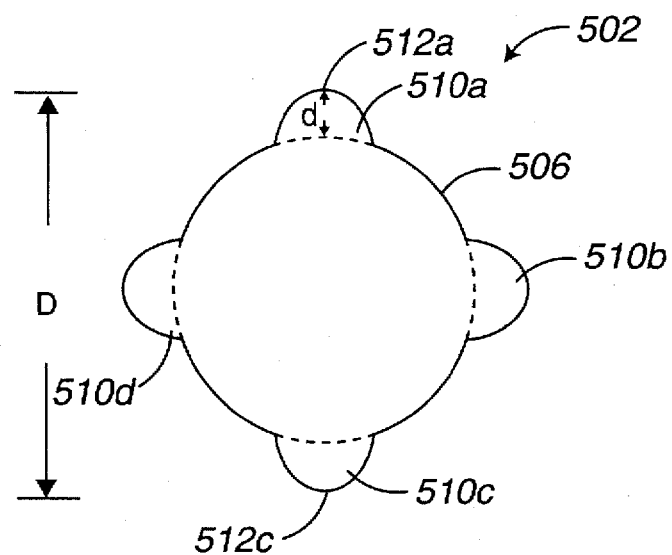
FIG. 5a is a diagrammatic cross-sectional axial view of a conformally positionable antenna assembly after a first molding process in accordance with an embodiment of the present invention.
Figure 6:
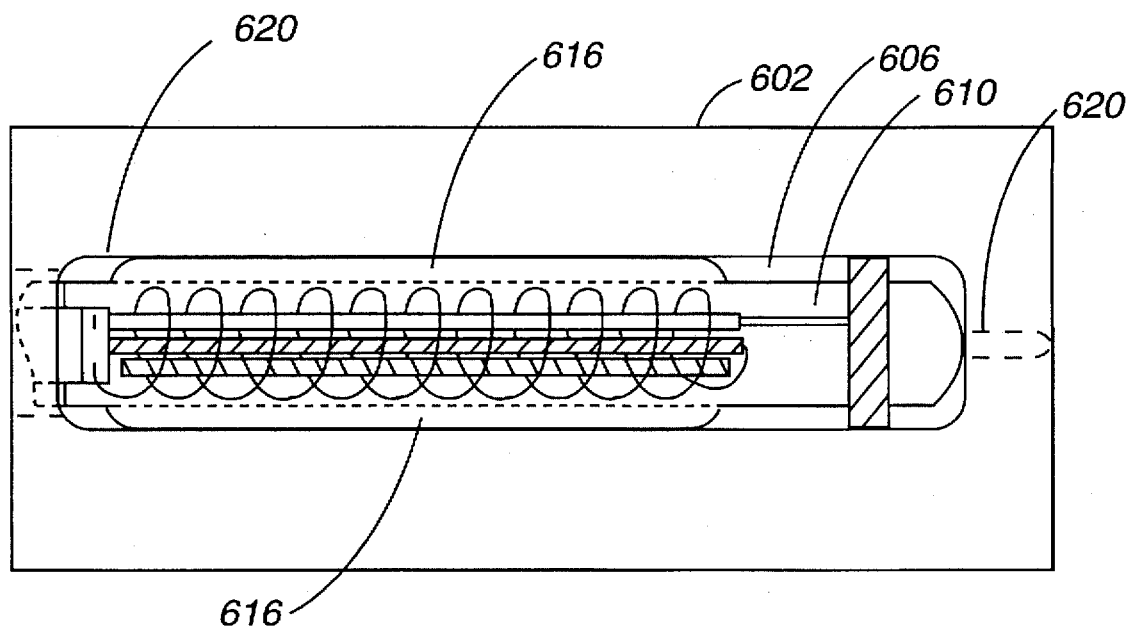
FIG. 6 is a diagrammatic top view of a second mold used to create an anchoring tip extension and a desired catheter tip diameter for an ablation catheter in accordance with an embodiment of the present invention.

Referring next to FIG. 5a, a diagrammatic cross-sectional axial view of a partially molded conformally positionable antenna assembly after a first molding process in accordance with an embodiment of the present invention will be described. It should be appreciated that the cross-sectional view is shown without an antenna coil, a sensor conduit, a shape memory wire and transmission line for illustrative purposes. That is, only the "outline" of conformally positionable antenna assembly 502 is shown for ease of illustration. Further, the cross-section of antenna assembly 502 that is shown is away from the extension plug formed at the distal end of antenna assembly 502. The "main body" 506 of antenna assembly, which is comprised of any suitable malleable material, as for example silicone as described above, encapsulates the antenna coil, sensor conduit, shape memory wire, etc. Although main body 506 may have any cross-sectional shape, in the embodiment as shown, main body 506 has a circular cross-section. Positioning ribs 510, which are used to position antenna assembly 502 within a second mold used to complete the antenna tip assembly as will be described below with reference to FIG. 6, are formed along the perimeter of main body 506, and are made of the same material as main body 506. The tip-to-tip distance D from the tip of a first positioning rib, as for example positioning rib 510a with tip 512a, to the tip of a second positioning rib which is directly opposite the first positioning rib, as for example positioning rib 510c with tip 512c, is generally approximately equal to the desired diameter of the completed antenna tip (not shown).

Positioning ribs 510 may take on any suitable cross-section. However, positioning ribs 510 which have curved, e.g. semi-circular, axial cross-sections are preferable due to the fact that the final antenna tip assembly has a round cross-section. That is, the completed catheter assembly has a round cross-section. Hence, positioning ribs 510 have curved cross-sections for ease of manufacturability. As will be appreciated by those skilled in the art, utilizing positioning ribs 510 with axial cross-sections which are rectangular, for example, would have the tendency to require an end mill to "shave" the edges of the rectangle in order to achieve the desired diameter of the completed antenna tip.

Although any number and orientation of positioning tips 510 may be used, in the described embodiment, four positioning ribs 510 which are symmetrical about the perimeter of main body 510 are shown. This number and orientation of positioning ribs 510 have been shown to be effective in securely positioning antenna assembly 502 within the aforementioned second mold. Each positioning rib, as for example positioning rib 510a, has a "height," i.e. tip-to-base dimension, d in the range of approximately 0.005 to 0.01 inches, as for example approximately 0.007 inches.

Figure 5B:
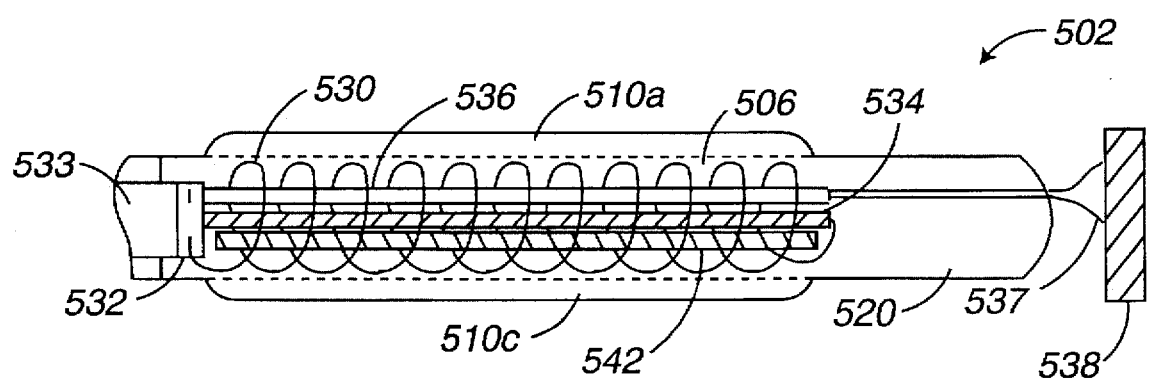

FIG. 5b a diagrammatic longitudinal side view of the partially molded conformally positionable antenna assembly of FIG. 5a. Antenna assembly 502 includes main body 506, an extension plug 520 formed at the distal end of antenna assembly 502, and positioning ribs 512. It should be appreciated that only two positioning ribs, i.e. positioning ribs 510a and 510c, have been shown for ease of illustration. Antenna assembly 530 includes, as previously described, an antenna coil 530, a sensor conduit 536, and a shape memory metal 542. Antenna coil 530 is coupled at a proximal end to the shield 532 of coaxial cable, or transmission line, 533 which effectively serves to ground antenna coil 530. At a distal end, antenna coil 530 is coupled to the center conductor 534 of coaxial cable 533. Sensor conduit 536 houses sensor wires 537 which are coupled to an electrode 538. Electrode 538, as shown, has not yet been mounted over extension plug 520. Although only one electrode 538 has been shown, it should be appreciated that the number of electrodes coupled to sensor wires 537, as well as the number of sensor wires 537, is dependent upon the requirements of a particular catheter.

Referring next to FIG. 6, the second mold used in forming a conformally positionable catheter will be described. FIG. 6 is a diagrammatic top view of the mold used to create a desired tip diameter and an anchoring tip extension for a catheter in accordance with an embodiment of the present invention. Mold 602 is used primarily to create the desired tip diameter for a conformally positionable catheter. Mold 602 is also used to eliminate any bubbles which may have formed in the dielectric material used in the first molding process described above with respect to FIGS. 4a and 4b. Mold 602 includes a main cavity 606 which holds the antenna assembly 610, as previously described with respect to FIGS. 5a and 5b, after the distal electrode of the antenna assembly has been properly mounted over the extension plug. Antenna assembly 610 will fit into main cavity 606, prior to the second injection molding process, substantially as shown. As the tip-to-tip distance between positioning ribs 616 is approximately equal to the final diameter of the catheter tip formed using mold 602, positioning ribs 616 is shown to be flush with the edges 620 of main cavity 606. The shape of main cavity 606 reflects the desired body shape of the completed antenna assembly.

An anchoring tip extension cavity 620 extends from main cavity 606 as shown. Anchoring tip extension cavity 620 is sized for the anchoring tip extension to be formed at the distal end of the completed catheter tip. That is, the shape of anchoring tip extension cavity 620, as well as the dimensions of anchoring tip extension cavity 620, are the desired shape and dimensions of the anchoring tip extension as shown in FIG. 2a.

Figure 7:
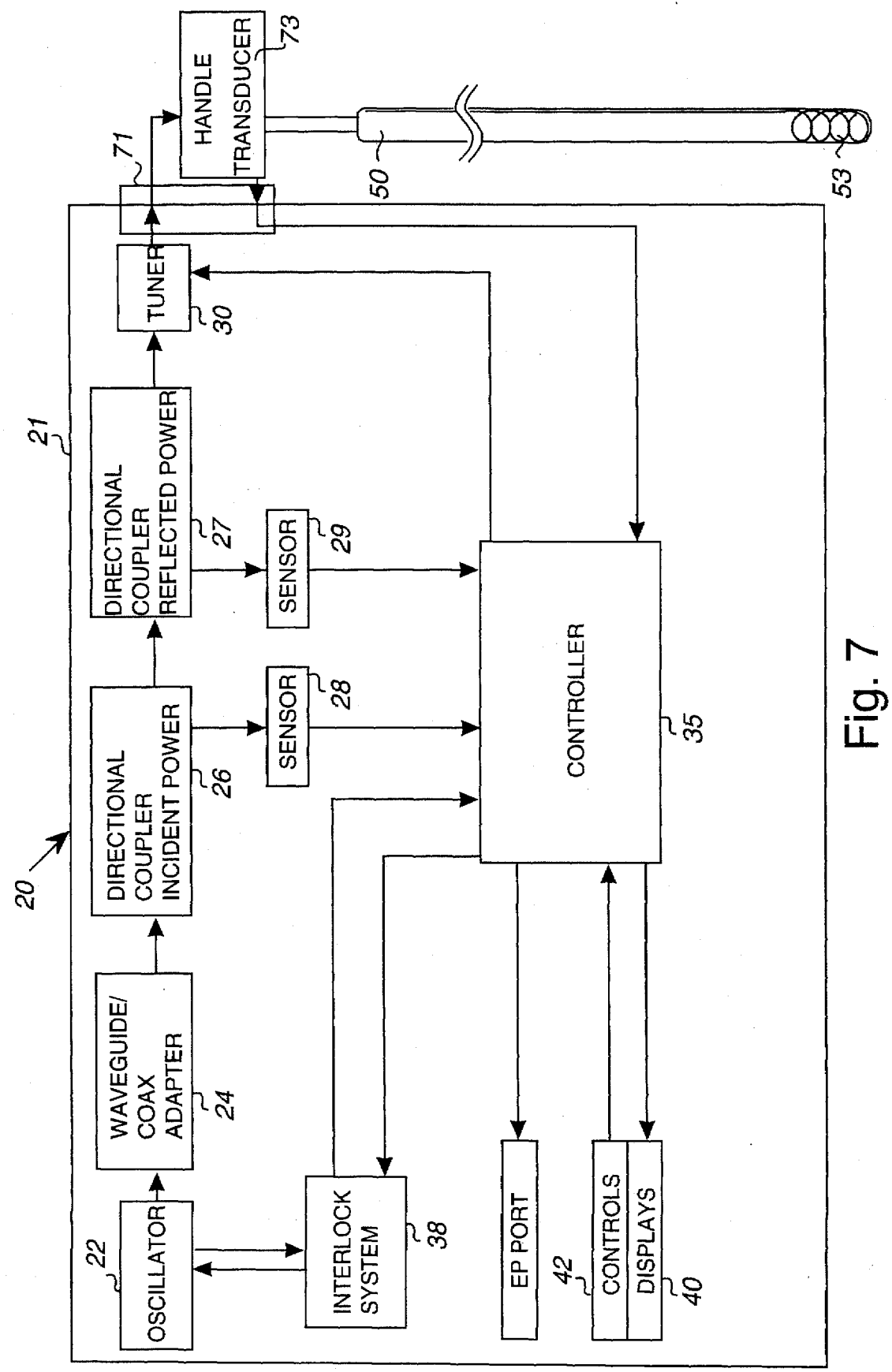
FIG. 7 is a diagrammatic illustration of a microwave ablation catheter system in accordance with an embodiment of the present invention.

A suitable microwave generator which may be used with the conformally positionable catheter will now be described. FIG. 7 is a diagrammatic illustration of a microwave ablation catheter system in accordance with an embodiment of the present invention. An ablation catheter system 10 generally includes a power supply 20 which is designed to generate controlled electromagnetic energy, a catheter 50 which is designed for insertion into a vessel (such as a coronary vessel) in the body of a patient and a connector 71 for coupling the power supply 20 to the catheter 50. As previously described with respect to FIG. 2a, the catheter typically includes a flexible outer tubing, a co-axial microwave transmission line that extends through the flexible tubing, and an antenna 56 coupled to the distal end of the co-axial transmission line. The connector couples transmission line 53 to external power supply 20. A handle 73 may be provided for use by the surgeon to facilitate steering and potentially other control functions. Additionally, catheter 50 may include a variety of sensors for monitoring the patient during insertion, positioning and/or use of the catheter 50. By way of example, such sensors may include a plurality of mapping electrodes 230, as shown in FIG. 2a, and one or more thermocouple wires (not shown). The co-axial microwave transmission line 53 includes a center conductor, a shield, and a dielectric material disposed between the center conductor and shield.

Although only a few embodiments of the present invention have been described, it should be understood that the present invention may be embodied in many other specific forms without departing from the spirit or scope of the present invention. By way of example, although the invention has been described in terms of a conformally positionable microwave ablation catheter for cardiac applications, it should be appreciated that the described conformally positionable microwave ablation catheter with a could be used for a wide variety of non-cardiac ablation applications as well.

The anchoring tip extension may be used to facilitate the positioning and stability of catheters which are not conformally positionable. That is, the anchoring tip extension may be used to anchor a catheter which does not include a shape memory metal. Further, the anchoring tip extension may serve to anchor conventional catheters, ablation or otherwise, without departing from the spirit or scope of the present invention.

While anchoring tip extension has been described as being formed by the second molding operation, it should be appreciated that anchoring tip extension may instead be formed during the first molding operation. Also, a combination of the previously described first and second molding operations may be used to form the anchoring tip extension such that the anchoring tip extension is partially formed in the first molding operation, and completed in the second molding operation.

Further, although two molding operations have been described as being used to form a conformally positionable microwave ablation catheter with an anchoring tip extension, it should be apparent that the use of any number of molding operations to form the catheter does not represent a departure from the spirit or the scope of the present invention. By way of example, a single molding operation may be used both to align the antenna assembly, to create the desired tip diameter of the ablation catheter tip, and to form the anchoring tip extension. Or, in some cases, three molding operations may be used to create a conformally positionable microwave ablation catheter with an anchoring tip extension. For example, the anchoring tip extension may be formed using a molding process intended only to form the anchoring tip extension. Therefore, the present examples are to be considered as illustrative and not restrictive, and the invention is not to be limited to the details given herein, but may be modified within the scope of the appended claims.

We claim:

1. An ablation catheter comprising:
   an elongated flexible tubular member adapted to be inserted into a vessel in the body of a patient, the flexible tubular member including a proximal portion and a distal portion, the distal portion having a first diameter;
   a transmission line disposed within the tubular member, the transmission line having proximal and distal ends, wherein the proximal end of the transmission line is suitable for connection to an electromagnetic energy source;
   a transducer coupled to the transmission line for generating an electric field sufficiently strong to cause tissue ablation; and
   a flexible anchoring tip extension immovably attached to and integrally formed with the distal portion of the catheter, the anchoring tip extension being more flexible than the distal portion of the elongated flexible tubular members wherein the anchoring tip extension is not arranged to penetrate a body wall of the patient during use.

2. An ablation catheter as recited in claim 1 wherein the anchoring tip extension has a diameter that is smaller than the diameter of the distal portion of the elongated flexible tubular member.

3. A catheter as recited in claim 2 further comprising a distal tip portion of the flexible tubular member, wherein the distal tip portion is formed from a silicone material that encapsulates the transducer.

4. A catheter as recited in claim 3 wherein:

the anchoring tip extension is carried by the distal tip portion of the flexible tubular member; and the anchoring tip extension is formed form the silicone material which forms the distal tip portion.

5. A catheter as recited in claim 1 wherein:

the distal portion of the flexible tubular member has a diameter of at least 0.07 inches;

the anchoring tip extension has a diameter in the range of approximately 0.05 to 0.07 inches; and the anchoring tip extension has a length in the range of approximately 0.08 to 0.5 inches.

6. A catheter as recited in claim 5 wherein:

the anchoring tip extension has a diameter of approximately 0.06 inches; and the anchoring tip extension has a length in the range of approximately 0.2 to 0.3 inches.

7. A catheter as recited in claim 1 wherein:

the transmission line is a co-axial cable; and the transducer is a helical antenna coil that is adapted to radiate electromagnetic energy in the microwave frequency range.

8. A catheter as recited in claim 1 further comprising a shape memory wire positioned within the antenna coil for straightening the distal portion of the elongated flexible tubular member after an ablation operation.

9. An ablation catheter comprising:

an elongated flexible tubular member adapted to be inserted into a vessel in the body of a patient, the flexible tubular member including a proximal portion and a distal portion, the distal portion having a first diameter;

a transmission line disposed within the tubular member, the transmission line having proximal and distal ends, wherein the proximal end of the transmission line is suitable for connection to an electromagnetic energy source;

a transducer coupled to the transmission line for generating an electric field sufficiently strong to cause tissue ablation; and a flexible anchoring tip extension immovably attached to the distal portion of the catheter, the anchoring tip extension having a diameter that is smaller than the diameter of the distal portion of the elongated flexible tubular member, wherein the anchoring tip extension is not arranged to penetrate a body wall of the patient during use.

10. A catheter as recited in claim 9 wherein:

the distal portion of the flexible tubular member has a diameter of at least 0.07 inches;

the anchoring tip extension has a diameter in the range of approximately 0.05 to 0.07 inches; and the anchoring tip extension has a length in the range of approximately 0.08 to 0.5 inches.

11. A catheter as recited in claim 10 wherein:

the anchoring tip extension has a diameter of approximately 0.06 inches; and the anchoring tip extension has a length in the range of approximately 0.2 to 0.3 inches.

12. A catheter as recited in claim 9 wherein the catheter is a microwave ablation catheter.

13. A catheter as recited in claim 12 wherein:

the transmission line is a co-axial cable disposed within the tubular member, the co-axial cable having proximal and distal ends, wherein the proximal end of the co-axial cable is suitable for connection to an electromagnetic energy source; and the transducer is a helical antenna coil coupled to the co-axial cable for generating an electric field sufficiently strong to cause tissue ablation.

14. A catheter as recited in claim 13 wherein:

the distal portion of the flexible tubular member is formed from a silicone material that encapsulates the helical antenna coil; and the anchoring tip extension is formed from the silicone material.

15. A catheter as recited in claim 14 wherein:

the helical antenna coil has an outer diameter in the range of approximately 0.07 to 0.1 inches;

the helical antenna coil has a length in the range of approximately 0.2 to 2.5 inches;

the anchoring tip extension has a diameter in the range of approximately 0.05 to 0.07 inches; and the anchoring tip extension has a length in the range of approximately 0.08 to 0.5 inches.

16. A catheter as recited in claim 15 wherein the microwave ablation catheter is an atrial fibrillation catheter.

17. A catheter as recited in claim 16 further comprising a shape memory wire positioned within the antenna coil wherein the shape memory wire is formed from a material selected from the group consisting of copper beryllium alloys, steel alloys, and nickel titanium.

18. A method for medical treatment using an ablation catheter system that includes a catheter having a transmission line disposed within a flexible tubular member, a transducer coupled to the transmission line at a tip portion of the catheter for generating an electric field sufficiently strong to cause tissue ablation, and a flexible anchoring tip extension immovably attached to and integrally formed with a distal portion of the catheter tip, the anchoring tip extension being more flexible than the tip portion of the catheter, the method comprising the steps of a) introducing the catheter into a patient's body such that the anchoring tip extension is lodged against but does not penetrate a wall of a cardiac chamber;

b) substantially conforming the tip portion of the catheter to the wall of the chamber with the anchoring tip lodged in place;

c) applying electromagnetic energy to the transmission line to cause ablation of cardiac tissue in a region adjacent the tip portion of the catheter;

d) repositioning the catheter tip, wherein during repositioning of the catheter tip the anchoring tip extension is dislodged from the wall of the chamber; and e) repeating steps (c) and (d) to facilitate the ablation of different regions of cardiac tissue.

19. A method as recited in claim 18 wherein introducing the catheter into a patient's body comprises:

monitoring electro-physiological signals using catheter electrodes;

determining an appropriate ablation position based at least in part on the monitored electro-physiological signals; and positioning the transducer at the determined appropriate ablation position.

20. A method as recited in claim 18 wherein microwave energy is applied to the transmission line to cause the ablation.

21. A method as recited in claim 18 wherein repositioning the catheter involves lodging the anchoring tip extension against the wall of the cardiac chamber.

* * * * *